United States Patent
Gauchel

(10) Patent No.: US 7,674,625 B2
(45) Date of Patent: Mar. 9, 2010

(54) METHOD FOR DETERMINING IMPROPER MANIPULATION OF URINE SAMPLES USING MARKER COMPOUNDS

(76) Inventor: Gisela Gauchel, Buschweg 1a, 51519 Odenthal-Volswinkel (DE)

( * ) Notice: Subject to any disclaimer, the term of this patent is extended or adjusted under 35 U.S.C. 154(b) by 913 days.

(21) Appl. No.: 10/535,230

(22) PCT Filed: Oct. 30, 2003

(86) PCT No.: PCT/EP03/12079

§ 371 (c)(1), (2), (4) Date: Feb. 16, 2006

(87) PCT Pub. No.: WO2004/046715

PCT Pub. Date: Jun. 3, 2004

(65) Prior Publication Data

US 2006/0154297 A1    Jul. 13, 2006

(30) Foreign Application Priority Data

Nov. 18, 2002   (DE) ................................ 102 53 664

(51) Int. Cl.
  *G01N 37/00* (2006.01)
(52) U.S. Cl. .................. 436/56; 436/127; 436/128; 436/140; 436/161
(58) Field of Classification Search .................. 436/164, 436/171, 175, 56
  See application file for complete search history.

(56) References Cited

U.S. PATENT DOCUMENTS

| 5,179,027 | A | | 1/1993 | Fisher |
| 5,756,067 | A | * | 5/1998 | Redgrave et al. ........... 424/1.81 |
| 6,068,981 | A | | 5/2000 | Rittenburg et al. |

FOREIGN PATENT DOCUMENTS

| WO | WO98/12557 | 3/1998 |
| WO | WO02/075307 | 9/2002 |
| ZA | 9306363 | 3/1994 |

OTHER PUBLICATIONS

Armand Quick, The Conjugation of Benzoic Acid in Man, J. Biol. Chem., vol. 92, pp. 65-85 (1931).*

* cited by examiner

*Primary Examiner*—Yelena G Gakh
(74) *Attorney, Agent, or Firm*—Gifford, Krass, Sprinkle, Anderson & Citkowski, P.C.

(57) ABSTRACT

The invention relates to a diagnostic method and to marker substances which enable manipulations in endogenic marking to be detected and thus prevented. According to the invention, a metabolizable substance is added to non-metabolizable marker substances, said metabolizable substance revealing a manipulation when detected in excreta.

2 Claims, 1 Drawing Sheet

PEG 300 + methyl-4-hydroxybenzoate

Figure 1:
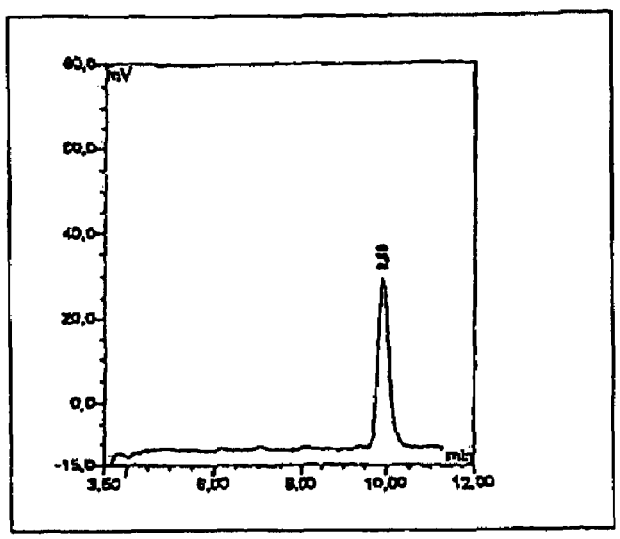

Nucleosil 300-C4 5μm, 125 mm x 4.6 mm, 33% CH₃OH/67%
H₂O, 0.5 ml/min.

Methyl-4-hydroxybenzoate

Nucleosil 300-C4 5µm, 125 mm x 4.8 mm, 33% $CH_3OH$/67% $H_2O$, 0.5 ml/min.

PEG 300 + methyl-4-hydroxybenzoate

Nucleosil 300-C4 5µm, 125 mm x 4.6 mm, 33% $CH_3OH$/67% $H_2O$, 0.5 ml/min.

METHOD FOR DETERMINING IMPROPER MANIPULATION OF URINE SAMPLES USING MARKER COMPOUNDS

The present invention relates to marker substances and their application in diagnostic methods.

Methadone and heroin programmes have been introduced for the treatment of drug-addicted patients. Test subjects taking part in them are forbidden to consume other illegal drugs and narcotics, and strict checks on additional consumption by urine tests are prescribed by law. Above all, the additional use of opiates and cocaine must be known in order to estimate the substitution requirement (S. T. Charmack et al., Drug Alcohol Depend 59 (2000) 43-49). Continuous additional drug use endangers the treatment goal of complete drugs abstinence, which includes the avoidance of acute withdrawal symptoms, the prevention of opiate-associated deaths, reduction of the infection risk with HIV and hepatitis viruses, protection of the population against drug supply criminality, rehabilitation and occupational reintegration. Above all, due to the increasing incidence of methadone-associated deaths (Commissioners of the Federal Government. Addiction and Drugs Report 2001. Federal Ministry for Family and Health, Berlin, April 2002), evidence of frequent additional use may lead to legally prescribed exclusion from the relevant substitution programme [Federal Medical and Health Insurance Commission: Guidelines of the Federal Medical and Health Insurance Commission on Substitution-Supported Treatment of Opiate Addicted Persons. Cologne 1999). Therefore there exists great interest on the part of drug-addicted persons to achieve falsely negative results from urine drug analysis. Normally, this can be achieved by excessive drinking for the purpose of strongly diluting the urine, by mixing in pre-analysis disrupter substances with a high falsification potential (S. L. Mikkelsen et al., Clin. Chem. 34 (1988) 2333-2336) or by substituting commercially available methadone-containing but drug-free urine for the subject's own urine. Each new drug testing method is immediately met by countermeasures from the drug world. The competition between the underworld and analytical testing is chronicled and can be followed in publications such as the periodical "High Times". One aim of drugs testing consists in recognising these imaginative and well-informed falsification and deception tactics and, if possible, to render them ineffective.

DE 101 12470 A1 describes a method for endogenous marking of mammals which is intended to enable unambiguous association of a bodily fluid—a secretion, a tissue sample or an excrement sample—with one individual. It consists in the oral or parenteral administration of only slightly or non-metabolisable substances and their subsequent analytical identification as such or in the form of its metabolites in the above sample materials. This concept has proved highly successful in routine clinical practice with polyethylene glycol (PEG) markers for monitoring drug-dependent test subjects undergoing methadone-substitution treatment. The subjects drink 100 ml of the methadone drink solution with marker substances added and provide their urine after a waiting time in the range of 30 min to 60 min. This is then centrifuged and analysed for Nucleosil C18, 3 µm, 125 mm×4.6 mm ID with a methanol-water mixture (44%/56%) using high pressure liquid chromatography at a flow rate of 0.5 ml/min. Sample preparation is undertaken automatically on-line using column switching to nucleosil C18 5 µm, 60 mm×4.6 mm ID, characterising of the markers in the eluate being carried out with refractive index detection (RID).

This method of endogenous marking is also susceptible to manipulation. It is rendered ineffective by subjects taking methadone as an out-patient in that they spit remains of the drink solution into drug-free urine, or squeeze out a cotton wool swab soaked in the mouth with drink solution into abused-drug-free urine.

This is the point at which the invention comes into use. It is therefore an object of the invention to provide a diagnostic method and marker substances used with it, by means of which manipulation may be discovered by means of endogenous marking. These should advantageously represent no added burden for the patient and also involve no additional costs for materials and personnel.

This aim is met through the diagnostic method according to claim 1 and the marker substances given in the subclaims.

In the method according to the invention, whereby a marker substance is administered to a test subject, said marker substance being identifiable in a bodily excretion, a metabolisable substance is additionally administered to the test subject.

Marker substances additionally administered to the test subject metabolise in the body such that they are no longer present in bodily excretions, such as urine. If the test subject should attempt to manipulate the allocation by spitting into the urine, the marker substance may be demonstrated there, such that a manipulation may be reliably prevented. For this reason, the term "spit marker" is an appropriate characterisation.

If metabolisable substances are mixed into the drink solution as spit markers which are not normally present in the urine, their presence there makes a falsification attempt reliably recognisable.

DE 101 12470 A1 mentions that samples may be taken from saliva. But the sample removal described there serves to identify illegally consumed substances and the allocation of the sample to an individual and cannot provide evidence of intended deception with regard to sample allocation.

Ideal spit markers are metabolisable substances which are permitted as additives in foods and pharmaceuticals. Following oral consumption, they are normally not present intact in the urine. An attempt at deception with regard to the analysis result is apparent if the substance used as a "spit marker" is found in the urine during marker analysis.

Advantageous spit marker substances are readily soluble in the drink solution. They have no pharmacological effect in the required concentrations, no evident colour and no strong flavour. During chromatography, they behave similarly to the other PEG markers.

Suitable spit marker substances are readily identifiable in the analysis and detection processes established in clinical chemical laboratories.

Possible spit marker substances are all the benzoic acid and 4-hyrdoxybenzoic acid derivatives, in particular their alkyl esters, acetic acid esters, fatty acid esters, lactic acid esters and tartaric acid esters of glycerol, propylene glycol esters of the fatty acids, monoglycerides and diglycerides of the edible fatty acids, sugar esters of the fatty acids, butylated hydroxyanisole and butylated hydroxytoluene, hexamethylene tetramine, amino acids, amino acid esters and all xanthine derivatives. Preferred marker substances are the Nipa esters methyl-, ethyl- and propyl-4-hydroxybenzoate permitted as preservatives. The methadone drink solution has to be preserved and if the above preservatives are used, no additional loading of the test subjects and no additional costs arise. Of the above preservatives, methyl-4-hydroxybenzoate (MHB) is the most suitable, since the chromatographic properties of this substance are very similar to those of the PEG markers. Elution takes place from the column together with the PEG markers and additional analysis steps are not necessary.

Methyl-4-hydroxybenzoate, also known as methylparaben and Nipagin-M®, is registered under the number E 218 as a food and pharmaceuticals additive (in the Rote Liste ["Red List"]). It is used, above all, for the preserving of pharmaceutical preparations such as eye drops, ointments and emulsions and, due to its low toxicity, is registered for the preserving of foods.

Apart from their use in methadone clinics, "spit markers" may also be used for endogenous marking in all areas of human and veterinary medicine where there exists a dishonest motivation to hide the origin of samples and in which the possibility exists of contaminating samples with the marker substance. All the groups of people given in the published application DE 101 12470 A1 who are prepared to practice deception may be checked in this manner. Examples are doping monitoring in high performance sports and in animal competitions, monitoring of road traffic and passenger transport, monitoring of continued drug freedom for renewal of a driving licence, employment examinations (Reagan decree), personnel medical examinations and veterinary check-ups.

Analysis of the spit markers takes place within the context of endogenous marking together with PEG markers by means of high pressure liquid chromatography and subsequent RI detection. Methyl-4-hydroxybenzoate has only a small refractive index, but an adequate absorption coefficient at 256 nm. If a UV detector is arranged in series with the RI detector, the loading of test subjects may be reduced by a factor of >10. All the marker signals in the chromatogramme are evaluated by means of the retention times determined from standard and reference chromatogrammes.

EXAMPLE

By means of an example, it will be explained how, when endogenous marking is used, attempts at deception are prevented.

100 ml methadone drink solution containing 1-3 g PEG marker mixture and preserved with 0.01% (10 mg/100 ml) methyl-4-hydroxybenzoate is administered to a test subject. The analysis is carried out according to the regulations contained in the published application DE 101 12470 A1. After 30-60 minutes, the test subject provides some urine. The eluate is additionally measured, after passing the RI detector, by a UV detector connected in series at $\lambda$=256 nm. A chromatogramme is produced in which the characteristic RID profile of the administered PEG marker is overlaid by the recording from the UV detector.

If the UV detector draws only a base line in the retention region of the spit marker and if the RI detector identifies the administered marker combination, the urine sample may be unambiguously allocated to the test subject concerned. If, however, the UV chromatogramme contains a peak at the retention time of the spit marker, it may be assumed that the test subject has deliberately added marker substance to an abused-drug-free urine sample with intent to deceive.

Figure 2:
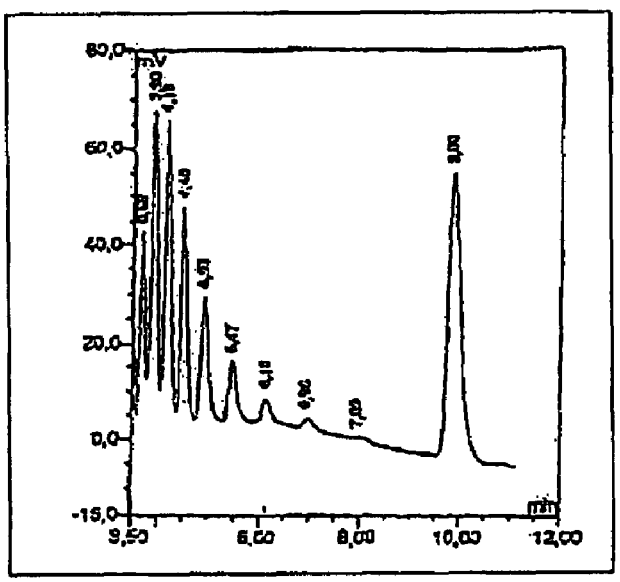

The drawings show two chromatogrammes in FIGS. 1 and 2, one for the spit marker, methyl-4-hydroxybenzoate alone (FIG. 1) and a second one together with the marker substance PEG 300 (FIG. 2).

If monodisperse PEG fractions are used as marker substances, it is advantageous with regard to the analysis speed to change the chromatographic system. If short-chained PEGs with shorter permeation times are preferred, the analysis for nucleosil 300-C4 5 μm, 125 mm×4.6 mm ID may be carried out with 33% $CH_3OH$/67% $H_2O$. Otherwise, the longer dwell time of the MHB during the stationary phase leads to extended analysis times.

The invention claimed is:

1. A method for determining improper manipulation of a urine sample by a test subject during testing, wherein prior to providing the sample, the subject is administered marker substances PEG (polyethylene glycols) that are only slightly metabolizable or are non-metabolizable and thus detectable in urine. comprising:
   administering to the test subject, at the same time and in addition to the PEG marker substances, a metabolizable substance comprising at least one of a derivative of benzoic acid or 4-hydroxy-benzoic acid, that can be detected in the same chromatogram with the non-metabolizable PEG marker substances and that, after metabolism, is no longer detectable iii the sample in which the marker substances are analyzed;
   collecting a urine sample from the test subject; and
   analyzing the urine sample with chromatography, wherein the detection of the metabolizable substance in the urine sample demonstrates improper manipulation by the test subject.

2. The method of claim 1, wherein methyl-4-hydroxybenzoate is used as the metabolizable substance.

\* \* \* \* \*